United States Patent [19]

Gallois et al.

[11] Patent Number: 4,493,937
[45] Date of Patent: Jan. 15, 1985

[54] 2-DIMETHYLAMINO-2-PARAHYDROX-YPHENYL SODIUM ACETATE, PREPARATION PROCESS AND APPLICATION THEREOF TO PRODUCTION OF PARAHYDROXYBENZYL CYANIDE

[75] Inventors: Philippe Gallois, Fosses; Yani Christidis, Paris, both of France

[73] Assignee: Societe Francaise Hoechst, Puteaux, France

[21] Appl. No.: 448,093

[22] Filed: Dec. 9, 1982

[30] Foreign Application Priority Data

Dec. 23, 1981 [FR] France .............................. 81 24104

[51] Int. Cl.$^3$ ............................................. C07C 99/00
[52] U.S. Cl. .................................. 562/444; 562/443; 562/414; 260/465 F
[58] Field of Search ................. 562/444, 443; 564/414

[56] References Cited

U.S. PATENT DOCUMENTS 3,778,463 12/1973 Gronowity et al. ................ 562/444
4,020,059 4/1977 Maeda et al. ....................... 564/414
4,175,206 11/1979 Senuma et al. ..................... 562/444
4,350,826 9/1982 Edwards et al. ................... 562/444

FOREIGN PATENT DOCUMENTS 2118988 11/1971 Fed. Rep. of Germany ...... 562/433
2131803 11/1972 France ............................... 562/433

OTHER PUBLICATIONS

Chem. Abst., vol. 55, #7743A, (1961).
Chemical Abstracts, vol. 84, No. 19, 10 mai 1976, p. 151, Resume No. 131504z, Columbus, Ohio (US) and JP-A-75 154 426 (Katsuda, Yoshio), (Dec. 12, 1975).

Primary Examiner—James H. Reamer
Attorney, Agent, or Firm—Karl W. Flocks

[57] ABSTRACT

The invention relates to crystallized 2-dimethylamino-2-parahydroxyphenyl sodium acetate, anhydrous or with 2 molecules of water. The process for preparation thereof comprises heating parahydroxy mandelic acid in dimethylformamide in the presence of a catalytic quantity of a strong acid, such reaction being followed by a sodium hydroxide neutralization. Said product is applied to the production of parahydroxybenzyl cyanide by reacting it with 2-hydroxy isobutyronitrile.

4 Claims, No Drawings

2-DIMETHYLAMINO-2-PARAHYDROXYPHENYL SODIUM ACETATE, PREPARATION PROCESS AND APPLICATION THEREOF TO PRODUCTION OF PARAHYDROXYBENZYL CYANIDE

This invention relates to crystallized 2-dimethylamino-2-parahydroxyphenyl sodium acetate anhydrous or with two molecules of water, as a novel industrial product, its process for preparation and the application thereof to the production of parahydroxybenzyl cyanide.

Crystallized 2-dimethylamino-2-parahydroxyphenyl sodium acetate anhydrous or with two molecules of water is not described in the literature. The French patent application No. 78 21174 published under number 2,431,405 teaches a process for having access to 2-amino-2-parahydroxyphenyl acetic acid or one of its N-alkylated or N,N-dialkylated derivatives, by reacting parahydroxy mandelic acid or one of its salts with ammonia or an alkylamine or a dialkylamine, or one of its salts, but such process advantageously carried out in aqueous solution requires long heating periods when it is operated at the ambient pressure:

30 hours at 103° C. according to Example 3, which may be substantially reduced by working under pressure; 4 hours at 135° C. under a pressure of 1.55 kg/cm$^2$ according to Example 4. These conditions associated with the handling of amines slightly condensed in carbon, volatile and irritating, render such process expensive and hardly adaptable to an industrial scale.

It has been now discovered that one can have easy and advantageous access to crystallized 2-dimethylamino-2-parahydroxyphenyl sodium acetate after heating the monohydrated parahydroxy mandelic acid in dimethylformamide in the presence of a catalytic quantity of a strong mineral acid.

The invention relates to the crystallized 2-dimethylamino-2-parahydroxyphenyl sodium acetate anhydrous or with two molecules of water.

The invention also relates to a novel process for obtaining with good yields the crystallized 2-dimethylamino-2-parahydroxyphenyl sodium acetate anhydrous or with two molecules of water, comprising the steps of heating parahydroxy mandelic acid in dimethylformamide in the presence of a catalytic quantity of a strong mineral acid such as concentrated sulfuric acid, then concentrating the reaction medium to about 50%.

At this stage, one can either filter the obtained suspension and collect the pure crystallized 2-dimethylamino-2-parahydroxyphenyl acetic acid which is later converted to its pure crystallized sodium salt anhydrous or with two molecules of water, or neutralize such suspension by adding the required quantity of sodium hydroxide in aqueous solution and continue the concentration under vacuum to dryness; in this case, the crystallized 2-dimethylamino-2-parahydroxyphenyl sodium acetate with two molecules of water is obtained, contaminated with traces of sodium salts of the starting parahydroxymandelic acid untransformed and of the strong mineral acid used as the catalyst. The strong mineral acid used as catalyst is advantageously concentrated sulfuric acid.

The 2-dimethylamino-2-parahydroxyphenyl acetic acid is a colourless crystallized product having an instantaneous melting point at about 260° C. with decomposition, a pKa of 2, and a very good solubility in water. In the crystallized state it is in form of dipolar ion, as shown by the infra-red spectra recorded in the solid state. The 2-dimethylamino-2-parahydroxyphenyl acetic acid also provides a colourless crystallized hydrochloride having an instantaneous melting point of 205°–210° C. (decomposition) and excellent solubility in water.

The pure crystallized 2-dimethylamino-2-parahydroxyphenyl sodium acetate anhydrous or with two molecules of water is obtained by dissolving 2-dimethylamino-2-parahydroxyphenyl acetic acid in the theoretical quantity of N sodium hydroxide followed by a dry concentration under vacuum.

The pure crystallized 2-dimethylamino-2-parahydroxyphenyl sodium acetate with two molecules of water is obtained by taking up again the crystallized residue obtained with acetone, dewatering and drying under vacuum at 40° C. at constant weight. The pure crystallized anhydrous salt is prepared by drying pure crystallized salt with two molecules of water under vacuum at a constant weight at 100° C.

The invention finally relates to the application of 2-dimethylamino-2-parahydroxyphenyl sodium acetate to the production of parahydroxybenzyl cyanide.

The parahydroxybenzyl cyanide is a commercial product often described in the literature. It is a precious intermediary to get access to various industrial products such as tyramine.

According to the invention, parahydroxybenzyl cyanide is advantageously obtained by reacting 2-dimethylamino-2-parahydroxyphenyl sodium acetate with acetone cyanhydrine (2-hydroxy-isobutyronitrile) and distilling the released acetone as it is being formed; a practical method is thus available for following the progress of the reaction. Such reaction is advantageously conducted hot in dimethylformamide. At the end of the reaction the parahydroxybenzyl cyanide is isolated from the reactional medium according to means known in themselves; advantageously, it is extracted with a $C_2$–$C_4$-alkyl acetate (such as butyl acetate) from the cooled reactional medium, it is diluted with water and the pH is brought to 4 with acetic acid.

Through evaporation of the extraction solvent the crystallized parahydroxybenzyl cyanide is obtained; then, if necessary it may be purified through rectification under vacuum.

The invention is illustrated by the following non limiting examples:

EXAMPLE 1

A solution of 1 mole of monohydrated parahydroxy mandelic acid is heated for 150 mm at 135° C. in 13 mols of dimethylformamide and 0.1 mole of concentrated sulfuric acid (d=1.83). The suspension so obtained is then concentrated under vacuum to half its initial volume, then it is cooled to the ambient temperature. The crystallized product formed is dewatered, washed by impasting it with one volume of methanol, then it is dried under vacuum at 100° C. at constant weight.

Thus, there is obtained 162 g of pure crystallized 2-dimethylamino-2-parahydroxyphenyl acetic acid having an instantaneous melting point of 260° C. with decomposition, i.e. a yield of 83% as compared to the theoretical value. Such acid is soluble in water, in diluted bases and in diluted acids; it is insoluble in methanol and acetone. Microanalysis:

|  |  | C % | H % | N % |
|---|---|---|---|---|
| $C_{10}H_{13}NO_3$ | calculated | 61.53 | 6.71 | 7.17 |
| M.W. = 195.21 | found | 61.2 | 6.8 | 7.0 |

Infra-red (KBr pellet): wide strips at about 1400 cm$^{-1}$ and 1600 cm$^{-1}$: characteristic strips of carboxylate ion.

Through concentration of mother waters to half quantity there is isolated a second crop of 25 g of crystallized 2-dimethylamino-2-parahydroxyphenyl acetic acid having an instantaneous melting point of 260° C. with decomposition, without depression, in admixture with pure crystallized 2-dimethylamino-2-parahydroxyphenyl acetic acid. The overall yield of the reaction is thus evaluated to 95.8% of the theoretical value, calculated with respect to the parahydroxy mandelic acid used.

Such acid provides a hydrochloride which crystallizes in methanol. It is very soluble in water, slightly soluble in methanol and insoluble in the diethyl oxide. It has a little sharp melting point. Microanalysis:

|  |  | C % | H % | N % | Cl % |
|---|---|---|---|---|---|
| $C_{10}H_{13}NO_3$, HCl | calculated | 51.83 | 6.09 | 6.05 | 15.31 |
|  | found | 51.5 | 6.1 | 6.1 | 15.2 |

39 g (0.2 mole) of pure crystallized 2-dimethylamino-2-parahydroxyphenyl acetic acid is dissolved in 200 cm$^2$ of N sodium hydroxide. The limpid solution obtained having a pH of 10.1 is then concentrated under vacuum to dryness and thereafter, the crystallized residue is impasted with acetone, filtered and dried under vacuum at 40° C. at constant weight; thus, there is obtained 49.4 g (0.195 mole) of pure crystallized 2-dimethylamino-2-parahydroxyphenyl sodium acetate with two molecules of water, i.e. a yield of 93% of the theoretical value. Microanalysis

|  |  | C % | H % | N % | $H_2O$ %[1] |
|---|---|---|---|---|---|
| $C_{10}H_{12}N\,NaO_3$, $2H_2O$ | calculated | 47.42 | 6.37 | 5.53 | 14.23 |
| M.W.: 253.24 | found | 47.2 | 6.5 | 5.4 | 13.7 |

[1]Determined by K. Fischer's method.

Potentiometric dosage:
free amine: 3.93 meq/g, i.e. 99.4% of the theoretical value,
carboxylate anion: 3.92 meq/g, i.e. 99.2% of the theoretical value,
carboxylic function: pKa=2,
ammonium function: pKa=8.8,
phenol function: pKa=10.5.

EXAMPLE 2

0.265 mole (22.47 g) of 98±1% of 2-hydroxy isobutyronitrile (acetone cyanhydrine) is introduced dropwise in 4 hours into a solution of 0.22 mole (55.84 g) of pure crystallized 2-dimethylamino-2-parahydroxyphenyl sodium acetate with two molecules of water in 3.25 moles (250 cm$^2$) of dimethylformamide heated to 135° C. The formed acetone is distilled as the reaction progresses. Heating at 135° C. is continued for 2 hours after completing the introduction of acetone cyanhydrine, then the reactional medium cooled to the ambient temperature is diluted with 1 l of water, brought to a pH=4 with acetic acid, and extracted 3 times with 1 l of butylacetate.

The joined organic phases are then washed twice with 1 l of water, dried on anhydrous sodium sulfate, filtered, then dry concentrated under vacuum. Thus, there is isolated 26 g (0.195 mole) of crystallized parahydroxybenxyl cyanide having a melting point of 70° C. (literature: Beil., 10, 191, M.P.=69°-71° C.), i.e. a yield of 89% of the theoretical value calculated relative to pure crystallized 2-dimethylamino-2-parahydroxyphenyl sodium acetate with two molecules of water, implemented.

It will be understood that this invention was only described in a merely explanatory, not at all limiting manner, and that any useful modification thereof can be effected without however departing from its scope as defined in the appended claims.

We claim:

1. A process for preparing a crystallized 2-dimethylamino-2-parahydroxphenyl acetic compound comprising hot reacting parahydroxymandelic acid with an excess of dimethylformamide in the presence of a catalytic quantity of a strong acid and crystallizing the resulting product whereby pure crystallized 2-dimethylamino-2-parahydroxyphenylacetic acid is obtained, and reacting said product with a hydrochloride agent whereby the corresponding hydrochloride compound is obtained; or reacting said acid product with sodium hydroxide and crystallizing the resulting product whereby the corresponding sodium crystallized acetate is obtained.

2. A process according to claim 1 comprising reacting between 110° and 140° C. one mole of anhydrous or monohydrated parahydroxymandelic acid with about 13 moles of dimethylformamide in presence of a catalytic quantity of concentrated sulfuric acid, half-concentrating the resulting suspension under vacuum and separating the resulting product by filtering whereby said crystallized 2-dimethylamino-2-parahydroxyphenylacetic acid is obtained, and then reacting said acid product with sodium hydroxide whereby said crystallized 2-dimethylamino-2-parahydroxyphenyl sodium acetate is obtained in anhydrous form or hydrated with 2 molecules of water.

3. A process according to claim 1 for the preparation of crystallized 2-dimethylamino-2-parahydroxyphenyl sodium acetate, wherein said hot reacting parahydroxymandelic acid with an excess of dimethylformamide in the presence of a catalytic quantity of a strong acid is effected by heating the reaction mixture to a temperature between 110° and 140° C., said strong acid catalyst being a strong mineral acid; the reaction medium is then concentrated; and said acid product of 2-dimethylamino-2-parahydroxyphenylacetic acid is then subjected to said reaction with sodium hydroxide to obtain crystallized 2-dimethylamino-2-parahydroxyphenyl sodium acetate with 2 molecules of water.

4. A process for preparing anhydrous crystallized 2-dimethylamino-2-parahydroxyphenyl sodium acetate comprising drying the hydrated product of claim 3, under vacuum at approximately 100° C.

* * * * *